United States Patent [19]

Levy

[11] Patent Number: 4,576,155

[45] Date of Patent: Mar. 18, 1986

[54] EXTERNAL PULMONARY BRACE AND METHOD FOR USING SAME

[75] Inventor: Aaron I. Levy, Chicago, Ill.

[73] Assignee: Thomas G. Baffes, Skokie, Ill. ; a part interest

[21] Appl. No.: 549,880

[22] Filed: Nov. 9, 1983

[51] Int. Cl.⁴ ............................................. A61F 13/00
[52] U.S. Cl. .................................. 128/132 R; 128/134
[58] Field of Search ............... 128/132 R, 133, 132 D, 128/134

[56] References Cited

U.S. PATENT DOCUMENTS

| | | | |
|---|---|---|---|
| 2,538,469 | 1/1951 | O'Brien | 128/133 |
| 2,547,466 | 3/1951 | Hoder | 128/134 |
| 3,324,851 | 6/1967 | Posner | 128/134 |
| 3,496,935 | 2/1970 | Bell, Jr. | |
| 3,724,846 | 4/1973 | Perrine | |
| 4,259,950 | 4/1981 | Klippel | |
| 4,321,890 | 3/1982 | Lange et al. | |

Primary Examiner—Stephen C. Pellegrino
Assistant Examiner—Karen L. Kaechele
Attorney, Agent, or Firm—Hill, Van Santen, Steadman & Simpson

[57] ABSTRACT

An external pulmonary brace has a pair of spaced brackets receiving and surrounding the tricep area of a user's upper arms, the brackets being connected to a central brace portion which extends across and substantially covers the user's chest. The central section and the brackets may be in the form of a unitary element, or the central section may be of elastic material joined to the brackets. By undertaking a downward movement of the upper arms toward the sides of the body, the patient may apply selected amounts of pressure to the chest area as needed to assist coughing or expectoration.

6 Claims, 5 Drawing Figures

EXTERNAL PULMONARY BRACE AND METHOD FOR USING SAME

BACKGROUND OF THE INVENTION

1. Field of the Invention

The present invention generally relates to medical braces, and more particularly relative to an external pulmonary brace for permitting a patient to apply selected pressure to the chest area to assist the patient in coughing or expectorating.

2. Description of the Prior Art

Postoperative patients who have undergone chest surgery generally experience pain when engaging in postoperative pulmonary ventilation, such as coughing or expectorating, and are additionally subject to the danger of disrupting the chest incision by such action. Standard postoperative procedures for assisting the postoperative patient generally involve the use of applied pressure by the nursing staff, such as by placing a pillow over the patient's chest and pressing downwardly. This method is burdensome to the hospital staff in that nurses must be removed from their other duties to assist the patient, and moreover the method is somewhat uncomfortable to the patient in that he or she does not have control over the exact amount of pressure being applied.

Various types of surgical restraints and braces are known, each of which exhibit a central section placed in contact with a portion of a patient's body, the central section being connected at opposite sides to brackets. Such a restraint is disclosed, for example, in U. S. Pat. No. 4,321,890 for use with an anesthetized animal during surgery. The animals limbs extend through V-shaped legs at opposite sides of the restraint with the body of the animal resting in a supine position therebetween to prevent the animal from rolling over during surgery and during postoperative recovery. A leg support is disclosed in U.S. Pat. No. 3,496,935 having an adjustable central section extending across a user's thighs, and to depending side members surrounding the sides of the user's legs to maintain the user's legs adjacent to each other.

An extrication back brace is disclosed in U.S. Pat. No. 4,259,950 for stabilizing the pelvic area, the illiac crest, the shoulder area and the head of an accident victims body has, when viewed in cross section, a contoured central portion flanked on each side by curved flanges 23.

A lifting yoke and harness is disclosed in U.S. Pat. No. 3,724,846 for positioning the biceps and triceps muscles of a weight lifter in a substantially vertical position when the user's forearms assume a substantially horizontal position while lifting a weight. The yoke has a narrow central portion extending across the user's chest and two straight terminal ends extending from each side thereof which are positioned behind the user's triceps.

SUMMARY OF THE INVENTION

It is an object of the present invention to provide a pulmonary brace for use by a patient having undergone chest surgery, or having otherwise experienced injury to the chest area, to assist the patient in pulmonary ventilation during recovery.

It is a further object of the present invention to provide such a brace which supports the chest wall and thereby permits such pulmonary ventilation to be undertaken with a minimum of pain and with no damage to sutures closing the chest incision.

A further object of the present invention is to provide such a brace which can be utilized by the patient without the assistance of an attendant.

Another object of the present invention is to provide such a brace and method for using same which permits the patient to control the amount of pressure applied to his or her chest area.

The above objects are inventively achieved in a pulmonary brace having a pair of spaced brackets designed to underlie and surround the upper arms of the patient, with a resilient central section spanning the distance between the brackets and extending across and substantially covering the patient's chest. The patient by practicing a simultaneous downward movement of the upper arms toward the sides of the body, forces the central section against the chest area, thereby applying a selected pressure to the chest area for aiding in coughing or expectorating, while simultaneously supporting the chest wall so as to prevent tearing of any sutures, or further exacerbating existing injury to the chest area.

The central section of the brace and the brackets on each side thereof may be formed of resilient plastic, in which embodiment the entire brace may be a unitary structure with the brackets integrally connected to the central section. In another embodiment of the invention, the central section may be comprised of elastic material which is secured to the brackets, which in this embodiment may also be formed of plastic or any other suitable rigid material.

Although described herein primarily for functioning as a pulmonary brace, it will be understood that the brace disclosed and claimed herein, particularly the embodiment employing a central section comprised of elastic material, may also be utilized by a patient for applying selected pressure to areas of the body other than the chest area. For example, the brace may be utilized to apply controlled abdominal pressure, in which case the central section of the brace will be placed over the abdomen, and the lower arms, rather than the upper arms, of the patient will be received in the brackets. Pressure is still applied by a downward movement of the arms with the patient in a generally supine position.

DESCRIPTION OF THE PREFERRED EMBODIMENTS

Figure 1:
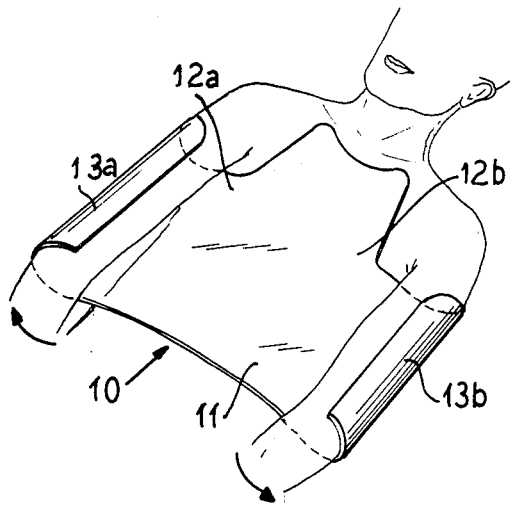
FIG. 1 is a perspective view showing an external pulmonary brace constructed in accordance with the principles of the present invention in place on a patient, and demonstrating the method for applying pressure to the chest area utilizing such a brace.

An external pulmonary brace 10 is shown in FIG. 1 in place over the chest area of a patient. The brace 10 has a central section 11 extending between and connected to two brackets 12a and 12b. The brackets 12a and 12b have respective curved sections 13a and 13b which receive and surround the upper rear or triceps area of the patient's arms.

Figure 2:
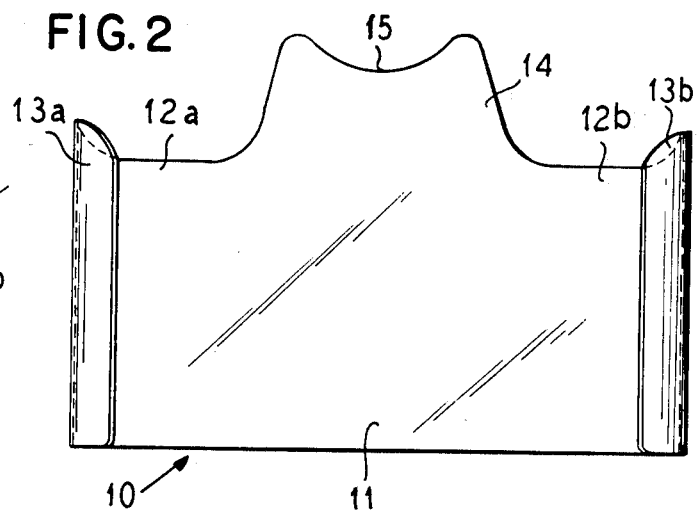
FIG. 2 is a front elevational view of a first embodiment of a pulmonary brace constructed in accordance with the principles of the present invention.
Figure 3:
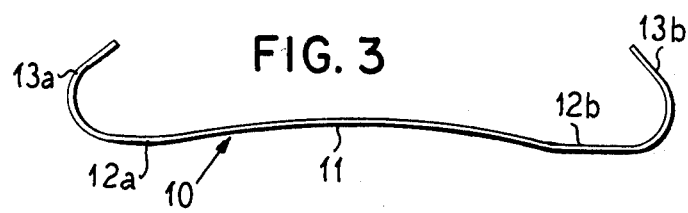
FIG. 3 is a plan view of the pulmonary brace shown in FIG. 2.

As shown in FIG. 2, the brace further has an upper section 14 contoured at 15 for accommodating the neck or clavicle region of the patient, providing further support for the chest area of the patient. As shown in FIG. 3, the central section 11 is bowed slightly outwardly, also for accommodating the patient's chest. When in place on a patient, as shown in FIG. 1, the central section 11 substantially covers the entire chest area of the patient, so as to support the chest wall during pulmonary ventilation, so as to assist the patient in such ventilation and simultaneously to protect sutures which may be present to close a chest incision from tearing. The support provided by the brace 10 not only minimizes the danger of tearing sutures, but also permits pulmonary ventilation to be undertaken while minimizing the possibility of worsening an existing injury to the chest.

The patient applies selected and controlled pressure to the chest area while in a generally supine position by moving his or her upper arms in a generally downward sweep, as indicated by the arrows in FIG. 1.

Figure 4:
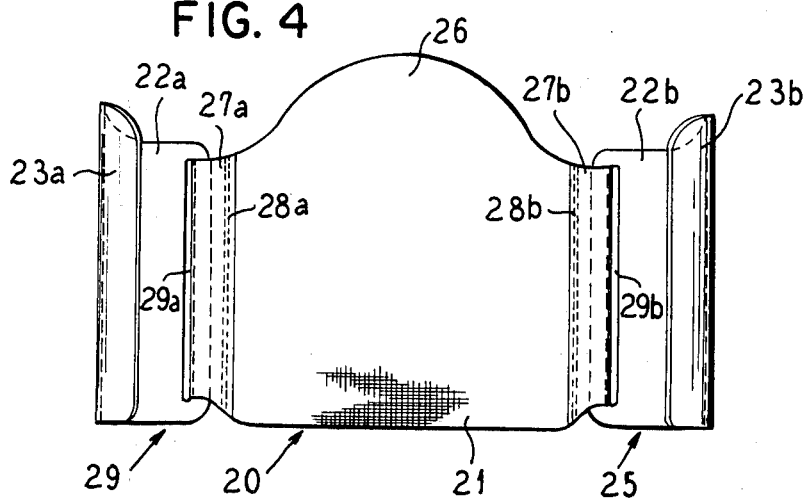
FIG. 4 is a front elevational view of a second embodiment of a pulmonary brace constructed in accordance with the principles of the present invention.
Figure 5:
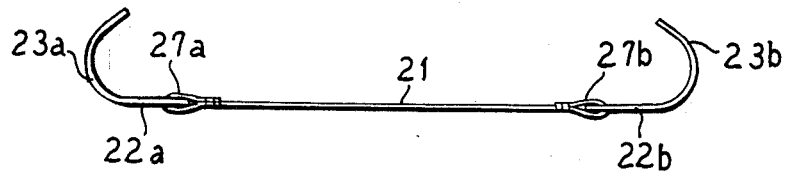
FIG. 5 is a plan view of the pulmonary brace shown in FIG. 4.

A further embodiment of the brace 20 is shown in FIG. 4. In this embodiment, the central section 21 is comprised of flexible elastic material. The brace 20, as the brace 10 described above, has brackets 24 and 25 on either side of the central section 21. The bracket 24 has a generally flat section 22a merging into a curved section 23a, which surrounds the tricep area of one of the arms of the patient. Similarly, the bracket 25 has a generally flat section 22b and a curved section 23b for surrounding the tricep area of the patient's other arm. The brackets 24 and 25 have respective slots 29a and 29b therein extending generally parallel to the curved portions 23a and 23b of the brackets. Flaps on either side of the central section 21 extend through the slots 29a and 29b and are folded so as to overlap the edges of the central section 21, thereby forming respective loops 27a and 27b surrounding respective portions of the brackets 24 and 25. The loops 27a and 27b are closed by respective fastening means 28a and 28b, such as by stitching.

The central section 21 has an upper section 26, corresponding to the section 14 in the unitary embodiment, which functions to cover a further portion of the chest area, thereby increasing the support afforded by the brace when utilized by a patient for applying pressure thereto.

Although modifications and changes may be suggested by those skilled in the art, it is the intention of the inventor to embody within the patent warranted hereon all changes and modifications as reasonably and properly come within the scope of his contribution to the art.

I claim as my invention:

1. An external brace for use by a patient for applying user-controlled pressure to a section of the patient's body comprising:
    a pair of spaced brackets respectively surrounding the patient's triceps;
    a central section consisting of elastic flexible material connected to each of and spanning the distance between said brackets, and extending across such substantially covering said body section to which pressure is to be applied;
    means connecting opposite sides of said central section to said spaced brackets;
    and said brackets and said central section being relatively disposed for applying selected pressure by the patient to said body section by effecting arm movement in a downward direction away from the patient's body pivoting the arms at the patient's body pivoting the arms at the patient's shoulders.

2. An external brace as claimed in claim 1 wherein said central section is adapted for extending across and substantially covering the chest area of a patient.

3. An external brace as claimed in claim 1 wherein each of said brackets has a slot therein, and wherein said means connecting said central section to said brackets comprises a loop of said elastic section at each side thereof extending through the aperture in the respective bracket, the free end of said loop overlapping said elastic section and being secured thereto.

4. An external pulmonary brace as claimed in claim 1 further comprising an extension of said central section extending from the patient's chest area toward the patient's neck for enlarging the area of the patient's body to which pressure is applied by movement of the patient's arms.

5. An external pulmonary brace for use by a patient for applying user-controller pressure to the chest area of the patient comprising:
    a pair of spaced brackets respectively receiving and substantially surrounding the triceps portion of the patient's arms; and
    a central section consisting of elastic flexible material connected to each of and spanning the distance between said brackets, said central section being adapted for extending across and substantially covering said chest area;
    means connecting opposite sides of said central section to said spaced brackets;
    said central section and said brackets being relatively disposed for applying controlled pressure to the patient's chest by the patient effecting arm movement in a downward direction away from the patient's body pivoting the arms at the patient's shoulder.

6. An external brace as claimed in claim 5 wherein each of said brackets has a slot therein, and wherein said means connecting said central section to said brackets comprises a loop of said elastic section at each side thereof extending through the aperture in the respective bracket, the free end of said loop overlapping said elastic section and being secured thereto.

* * * * *